(12) United States Patent
Dafni et al.

(10) Patent No.: US 7,949,089 B2
(45) Date of Patent: May 24, 2011

(54) APPARATUS AND METHOD FOR TRACKING FEATURE'S POSITION IN HUMAN BODY

(75) Inventors: Ehud Dafni, Caesarea (IL); Rafael Shmeul Brada, Hod-HaSharon (IL)

(73) Assignee: Arineta Ltd., Caesarea (IL)

( * ) Notice: Subject to any disclaimer, the term of this patent is extended or adjusted under 35 U.S.C. 154(b) by 1 day.

(21) Appl. No.: 12/419,801

(22) Filed: Apr. 7, 2009

(65) Prior Publication Data

US 2009/0257551 A1 Oct. 15, 2009

Related U.S. Application Data

(60) Provisional application No. 61/123,584, filed on Apr. 10, 2008.

(51) Int. Cl.
*H05G 1/00* (2006.01)
(52) U.S. Cl. .................................. 378/9; 378/6
(58) Field of Classification Search .............. 378/4–20, 378/41
See application file for complete search history.

(56) References Cited

U.S. PATENT DOCUMENTS

| 6,198,790 | B1 * | 3/2001 | Pflaum | 378/9 |
| 2005/0195935 | A1 * | 9/2005 | Yahata | 378/4 |
| 2009/0285355 | A1 * | 11/2009 | Brada et al. | 378/20 |

* cited by examiner

*Primary Examiner* — Hoon Song
(74) *Attorney, Agent, or Firm* — William H. Dippert; Eckert Seamans Cherin & Mellott, LLC

(57) ABSTRACT

A CT scanner for scanning a subject is provided, the scanner comprising: a gantry capable of rotating about a scanned subject; at least two cone beam X-Ray sources displaced from each other mounted on said gantry; at least one 2D detector array mounted on said gantry, said detector is capable of receiving radiation emitted by said at least two X-Ray sources and attenuated by the subject to be scanned; a first image processor capable of generating and displaying CT images of a volume within the subject; a second image processor capable of generating projection X-Ray images of said volume, wherein the images are responsive to X-Ray separately emitted by each of said at least two cone beam X-Ray sources; and a third image processor capable of generating and displaying fluoroscopic images composed of said projection X-Ray images, wherein said fluoroscopic images are spatially registered to said CT images.

46 Claims, 6 Drawing Sheets

APPARATUS AND METHOD FOR TRACKING FEATURE'S POSITION IN HUMAN BODY

CROSS-REFERENCE TO RELATED APPLICATION

This application claims the benefit of U.S. Provisional Patent Application Ser. No. 61/123,584, filed Apr. 10, 2008, the entire contents of which are incorporated by reference, as if fully set forth herein.

FIELD OF THE INVENTION

The invention relates to tracking position of organs, lesions or devices in the human body, and more specifically it to application of Computed Tomography (CT) and Stereoscopic Fluoroscopy imaging techniques during interventional procedures.

BACKGROUND OF THE INVENTION

Medical procedures that require tracking of the position of a lesion or device in the human body are very common. A lesion is referred to herein as a tumor, diseased artery or any other diseased or target tissue. For example, in percutaneous coronary intervention (PCI) procedures a balloon is inserted through a catheter from an artery in the groin to a narrowed section in a coronary artery. The balloon is then inflated, compressing the plaque and dilating the narrowed coronary artery so that blood can flow more easily. This is often accompanied by inserting an expandable metal stent.

The procedure is monitored by X-Ray imaging technique referred to as angiography, which combines fluoroscopic projection imaging of multiple images per second and infusion of contrast agent (also referred to as dye) to the arteries to be viewed. Using angiography, the physician can view and identify the narrowing in the artery, direct the balloon and stent to position and verify correct positioning of the stent.

However, conventional fluoroscopy or angiography provide 2D projection images and do not disclose the complete 3D structure underneath. The 3D structure of human organs can be viewed by techniques such as Computed Tomography (CT) or MRI.

CT scanners are used routinely in medical, homeland security and other fields. In a typical CT scanner there is an X-Ray source and array detector, both mounted on a gantry and made to rotate about a scanned subject. Radiation that was attenuated by the scanned subject is received by the detector, acquired and reconstructed to produce images of tomographic cross sections, also called "slices". The slice images are stored on computer media, displayed and optionally processed to 3D images.

CT scanners can acquire, reconstruct and display single or several slices in almost real time. However, CT scanners typically require minutes to scan a whole organ, reconstruct the slice images and process the data to 3D presentation. Therefore, CT scanners cannot typically be used for real time monitoring of position in three dimensions during interventional procedures.

One solution known in the art is to carry out a CT scan of the subject and generate volumetric images. Subsequently, in a different session using a different system, real time 2D fluoroscopy or other real time imaging is performed wherein the CT images are used as a guiding roadmap. Some exemplary clinical applications where combination of 2D fluoroscopy and 3D CT images may be beneficial are neural interventions and electrophysiology interventions such as RF ablation and lead placement procedures. The disadvantage is that the two sets of images are not acquired under identical conditions of the scanned subject and are not registered respective of each other in space, thereby limiting the accuracy.

CT scanners using a cone beam X-Ray source and a large area array detector are also known in the art. It has been noted that the large area CT detector can be used in association with the cone beam source to generate fluoroscopic or angiographic 2D images. Substantially the method involves positioning the gantry carrying the source and detector at a given rotation angle wherein the subject is in the radiation field, acquiring attenuation data, processing the data and displaying multiple 2D images per second.

U.S. Pat. No. 6,198,790 to Pflaum et al., the content of which is incorporated herein by reference, discloses an X-ray diagnostic apparatus having a computed tomography device including a first X-ray tube, which is fastened to a gantry ring and which emits a fan-shaped effective beam, and an opposed radiation receiver, which is formed by a row of individual detector elements, each of which forms an electrical signal corresponding to the received radiation intensity. A second X-ray tube is additionally fastened to the gantry ring at a right angle to the first X-ray tube, opposite which, at the gantry ring, a matrix-like X-ray detector is arranged. The second X-ray tube is activated in specified rotational positions in pulsed fashion, such as at the uppermost rotational point. X-ray shadowgraphs thus can be produced simultaneously with CT images and without a need for repositioning any of the apparatus components.

U.S. Pat. No. 7,164,745 to Tsuyuki, the content of which is incorporated herein by reference; discloses X-ray computed tomography apparatus for medical diagnosis, reconstructs tomographic image based on detection of X-rays penetrated through patient, and creates fluoroscopic image on plane that is perpendicular to X-ray path.

CT scanners using multiple cone beam sources are also known in the art. Multiple X-Ray sources may be distributed azimuthally about the rotation axis, or along an axis parallel to the rotation axis (Z axis), or both. Of interest to us are configurations wherein the sources are relatively close to each other and are irradiating a common detector array such that the multiple beams are at least partially overlapping.

Some disclosures that cover such geometries are application U.S. Publication No. 2006/285633 A1 to Sukovic et. al.; PCT Publication Nos. WO 2006/038145 A to Koken et al. and WO 2008/122971 A1 to Dafni, and which is assigned to the assignee of the present invention, the content of which is incorporated herein by reference.

It has been noted that overlapping beam from multiple X-Ray sources operating asynchronously can be used for stereoscopic visualization. Some disclosures are U.S. Pat. No. 5,233,639 to Marks; U.S. Pat. No. 4,819,255 to Sato; U.S. Pat. No. 4,712,226 to Horsbaschek; and U.S. Pat. No. 6,181,768 to Berliner, the contents therein are incorporated herein by reference. Several publications discuss X-Ray stereoscopic imaging in connection to angiography: "Machine precision assessment for 3D/2D digital subtracted angiography images registration", Proceedings of SPIE Medical Imaging 1998, K. Hanson Ed, vol 3338, pp. 39-49, 23-26 Feb. 1998, and "Application of Stereo Techniques to Angiography: Qualitative and Quantitative Approaches" Jean Hsuy et. al., Purdue University, all incorporated herein by reference.

However, devices incorporating the 3D imaging capabilities of CT scanners and stereoscopic fluoroscopy or angiography in the same system are not known in the art. It is the purpose of this invention to provide such a device and thereby gain the benefits of accurate spatial registration between the two sets of images, as well as the benefits of an efficient clinical workflow.

SUMMARY OF THE INVENTION

The invention relates to tracking position of organs, lesions or devices in the human body, and more specifically it to application of Computed Tomography (CT) and Stereoscopic Fluoroscopy imaging techniques during interventional procedures.

According to an aspect of the current invention, a CT scanner for scanning a subject is provided, the scanner comprising: a gantry rotor capable of rotating about a scanned subject; at least two cone beam X-Ray sources displaced from each other mounted on said gantry; at least one 2D detector array mounted on said gantry, said detector is capable of receiving radiation emitted by said at least two X-Ray sources and attenuated by the subject to be scanned; a first image processor capable of generating and displaying CT images of a volume within the subject; a second image processor capable of generating projection X-Ray images of said volume, wherein the images are responsive to X-Ray separately emitted by each of said at least two cone beam X-Ray sources; and a third image processor capable of generating and displaying fluoroscopic images composed of said projection X-Ray images, wherein said fluoroscopic images are spatially registered to said CT images.

In some embodiments, any of said first image processor, second image processor and third image processor are incorporated into a single image processor.

In some embodiments, the at least two X-Ray sources are displaced from each other along a direction parallel to the rotation axis of said gantry.

In some embodiments, said at least two X-Ray sources are displaced from each other azimuthally respective of the rotation axis of said gantry.

In some embodiments, said at least two X-Ray sources comprise two X-Ray sources.

In some embodiments, said two sources of the at least two X-Ray sources are operative for generating stereoscopic images.

In some embodiments, said fluoroscopic images are generated following injection of contrast agent.

In some embodiments, said fluoroscopic images are generated and displayed multiple times per second.

In some embodiments, said fluoroscopic images are generated and displayed one at a time.

In some embodiments, said fluoroscopic images are displayed overlaying an image derived from said CT images.

In some embodiments, said fluoroscopic images are displayed side by side with said CT images.

In some embodiments, a graphic mark indicating position of a feature within said volume is overlaid said CT images wherein said position of the feature within said volume is computed responsive to the position of the feature in said projection X-Ray images.

In some embodiments, said fluoroscopic images are used to position an interventional device respective of a lesion.

In some embodiments, said fluoroscopic images are displayed in stereoscopic form.

In some embodiments, said an algorithm is used to calculate the depth of a feature in said fluoroscopic images.

In some embodiments, the images are acquired responsive to heart monitor signal.

In some embodiments, said images are acquired responsive to breathing monitor signal.

In some embodiments, said multiple X-Ray sources comprise a single X-Ray tube housed within a single vacuum enclosure wherein said tube has multiple focal spots.

In some embodiments, said multiple X-Ray sources comprise multiple X-Ray tubes.

According to another aspect of the current invention, a method for tracking position of a feature in a subject is provided, the method comprising the steps of: operating a CT scanner to generate and display CT images of a volume within the subject; operating said CT scanner to generate projection X-Ray images of said volume wherein said images are responsive to X-Ray emitted by two X-Ray sources displaced from each other; and generating and displaying stereoscopic images from said projection X-Ray images, wherein said stereoscopic images are spatially registered to said CT images.

In some embodiments, the CT scanner comprises two X-Ray sources.

In some embodiments, the CT scanner comprises more than two sources wherein at least two sources are operative for generating stereoscopic images.

In some embodiments, the method further comprising injecting contrast agent to the subject.

In some embodiments, said stereoscopic images are generated and displayed multiple times per second.

In some embodiments, said stereoscopic images are generated and displayed one at a time.

In some embodiments, said stereoscopic images are displayed overlaying said CT images.

In some embodiments, said stereoscopic images are displayed side by side with said CT images.

In some embodiments, a graphic mark indicating position of a feature within said volume is overlaid said CT images wherein said position of the feature within said volume is computed responsive to the position of the feature in said projection X-Ray images.

In some embodiments, the method further comprising positioning an interventional device respective of a lesion or specific anatomic structure using said stereoscopic images.

In some embodiments, the method further comprises identifying the lesion or specific anatomic structure using CT images.

In some embodiments, the method further comprising verifying the position of said interventional device respective said lesion or specific anatomic structure using CT images, wherein the positioning process is guided by said stereoscopic images.

In some embodiments, the method further comprising acquiring images responsive to heart monitor signal.

In some embodiments, the method further comprising acquiring images responsive to breathing monitor signal.

According to yet another aspect of the current invention, a CT scanner for scanning a subject is provided, the scanner comprising:
a gantry stator;
a CT subsystem comprising:
at least one gantry rotor, mounted on said gantry stator capable of rotating about a scanned subject; a CT X-Ray source mounted on said at least one rotor; a CT X-Ray detector array mounted on said at least one rotor; wherein said CT X-Ray source and said X-Ray detector are configured to rotate together about said scanned subject, and wherein said CT detector array is capable of receiving radiation emitted by said CT X-Ray source and attenuated by the subject to be scanned; and a first image processor capable of generating and displaying CT images of a volume within the subject; and
a fluoroscopy subsystem comprising:

at least a first and a second cone beam X-Ray sources displaced from each other mounted on said at least one rotor; a 2D detector mounted on said on said at least one rotor, wherein said at least a first and a second cone beam X-Ray sources and said 2D detector array are configured to rotate together about said scanned subject, and wherein said 2D detector is capable of receiving radiation emitted by said at least first and second X-Ray sources and attenuated by the subject to be scanned; and a second image processor capable of generating projection X-Ray images of said volume, wherein the images are responsive to X-Ray separately emitted by each of said at least first and second cone beam X-Ray sources; and a third image processor capable of generating and displaying fluoroscopic images composed of said projection X-Ray images, wherein said fluoroscopic images are spatially registered to said CT images.

In some embodiments, the said CT subsystem and said fluoroscopy subsystem are mounted on the same gantry rotor.

In some embodiments, the said CT subsystem and said fluoroscopy subsystem are mounted substantially perpendicular to each other.

In some embodiments, the said at least one gantry rotor comprises a first and a second gantry rotors configured to independently rotate about said subject, and wherein said CT subsystem is mounted to said first gantry rotor, and said fluoroscopy subsystem is mounted on said second gantry rotor, and wherein said first and second gantry rotors are mounted on said gantry stator.

In some embodiments, said fluoroscopic images are displayed in stereoscopic form.

In some embodiments, a graphic mark indicating position of a feature within said volume is overlaid said CT images wherein said position of the feature within said volume is computed responsive to the position of the feature in said projection X-Ray images.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for understanding of the invention, the description taken with the drawings making apparent to those skilled in the art how the several forms of the invention may be embodied in practice.

Figure 1:
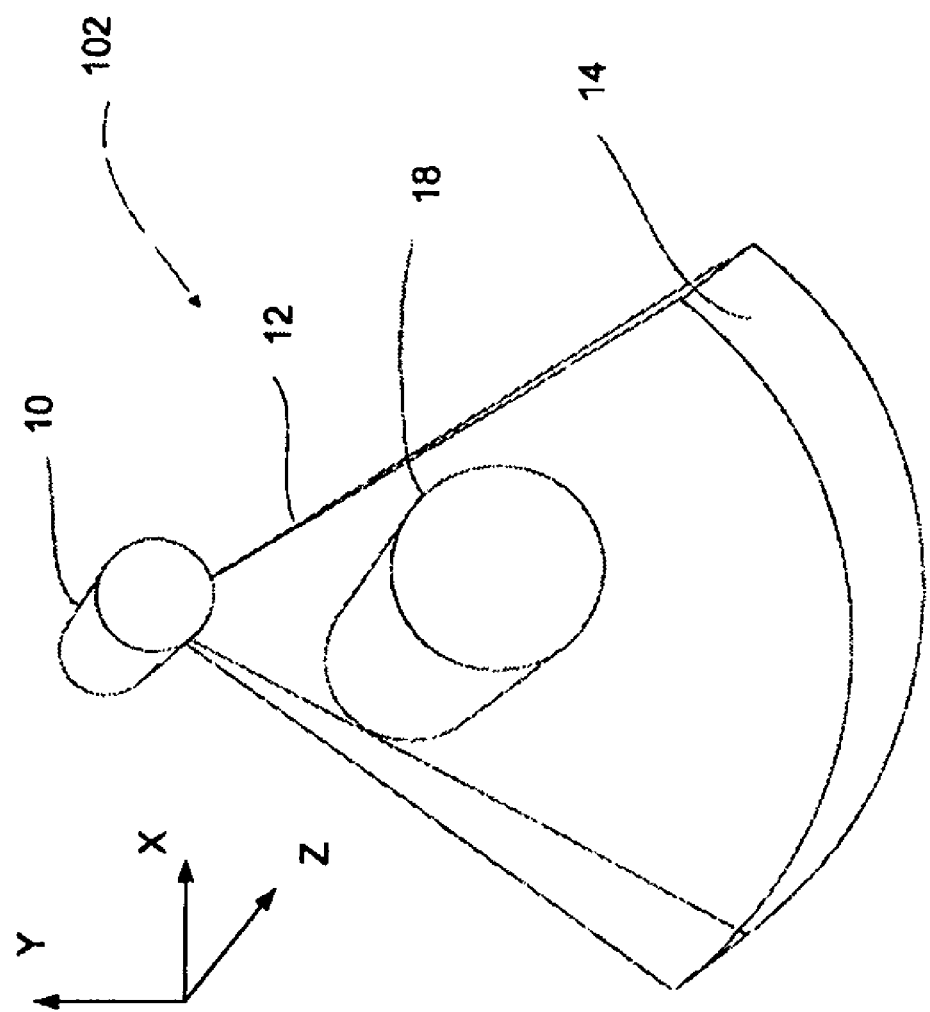

IN THE DRAWINGS:

FIG. 1 is an illustration of a prior art cone beam CT scanner.

Figure 2:
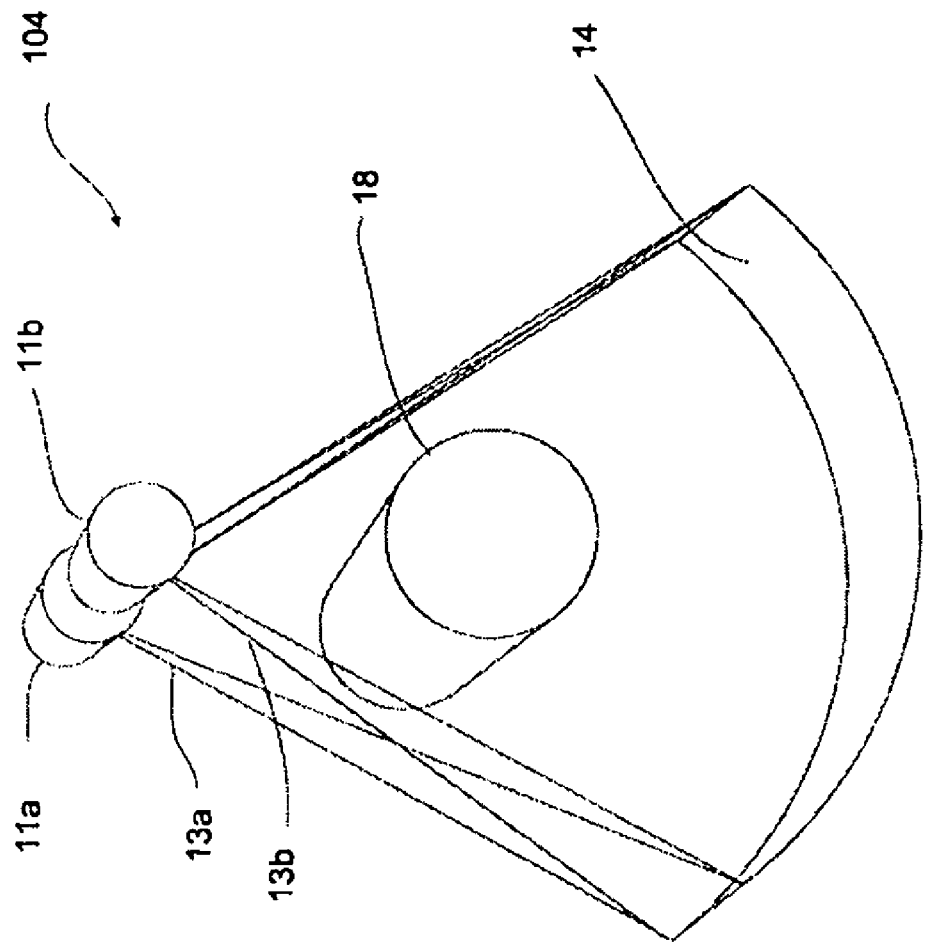

FIG. 2 is an illustration of a cone beam CT scanner having multiple X-Ray sources, wherein the sources are displaced from each other along the Z direction according to an exemplary embodiment of the current invention.

Figure 3:
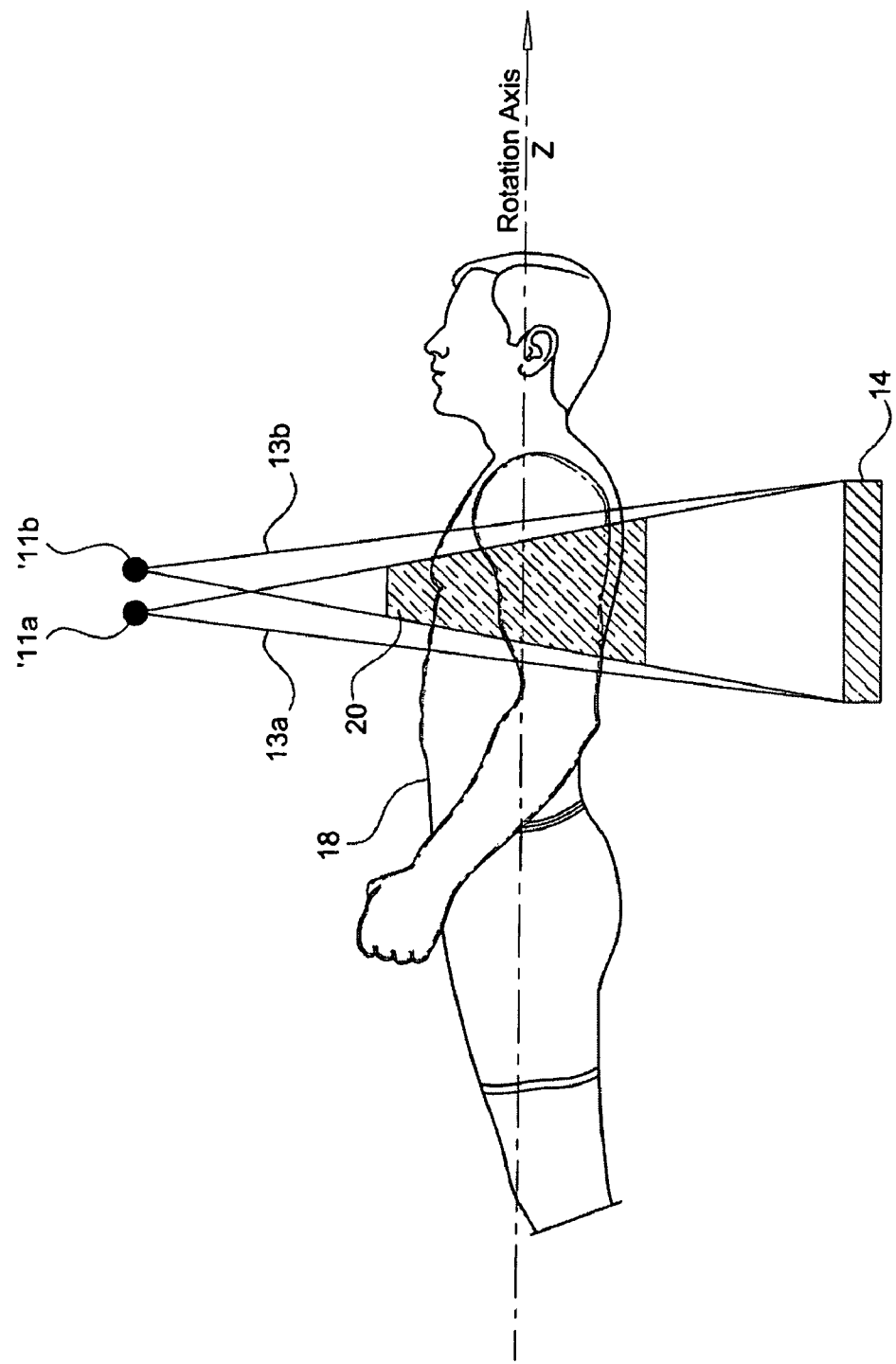

FIG. 3 is a side view of a cone beam CT scanner having multiple X-Ray sources, wherein the sources are displaced from each other along the Z direction according to an exemplary embodiment of the current invention, showing the scanned subject shown by a way of example a human patient undergoing imaging of the heart.

Figure 4:
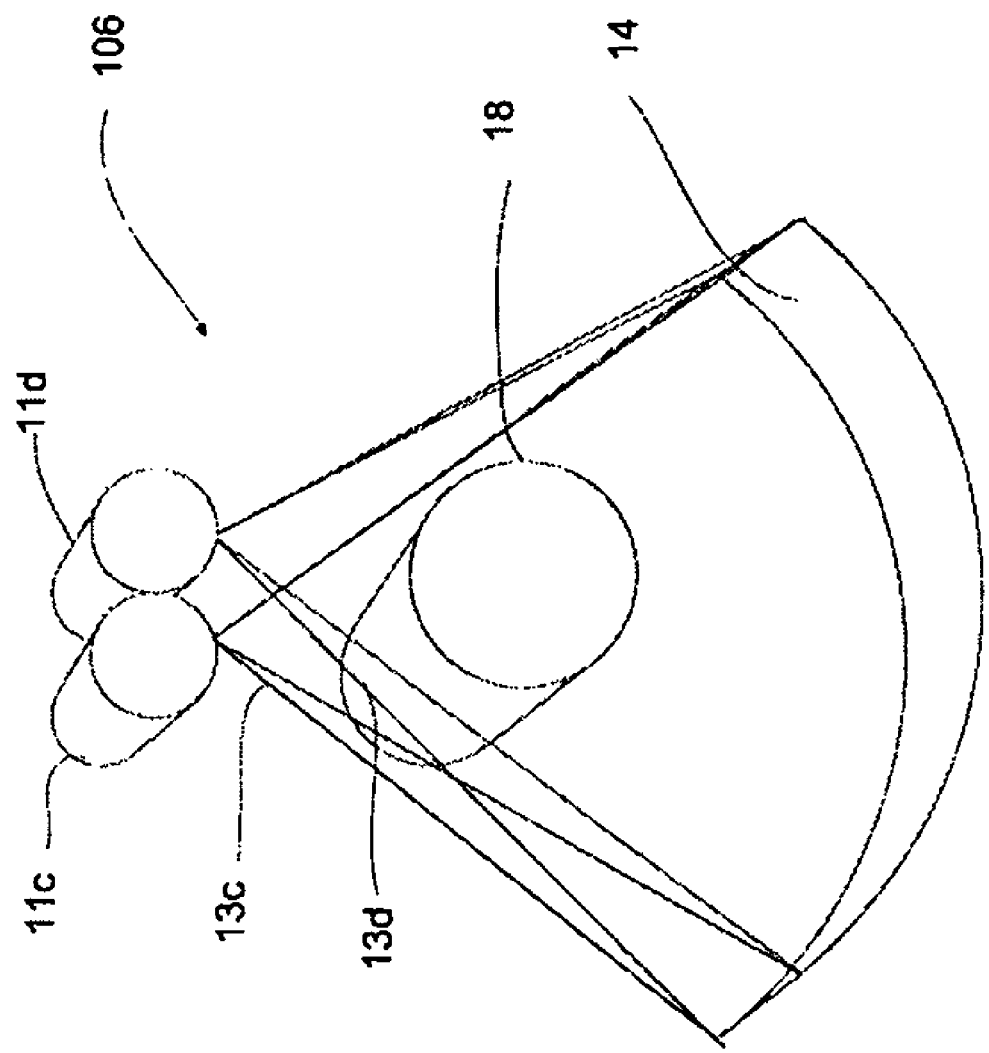

FIG. 4 is an illustration of a multiple X-Ray source cone beam CT scanner according to an exemplary embodiment of the current invention, wherein the sources are displaced from each other along the X direction.

Figure 5:
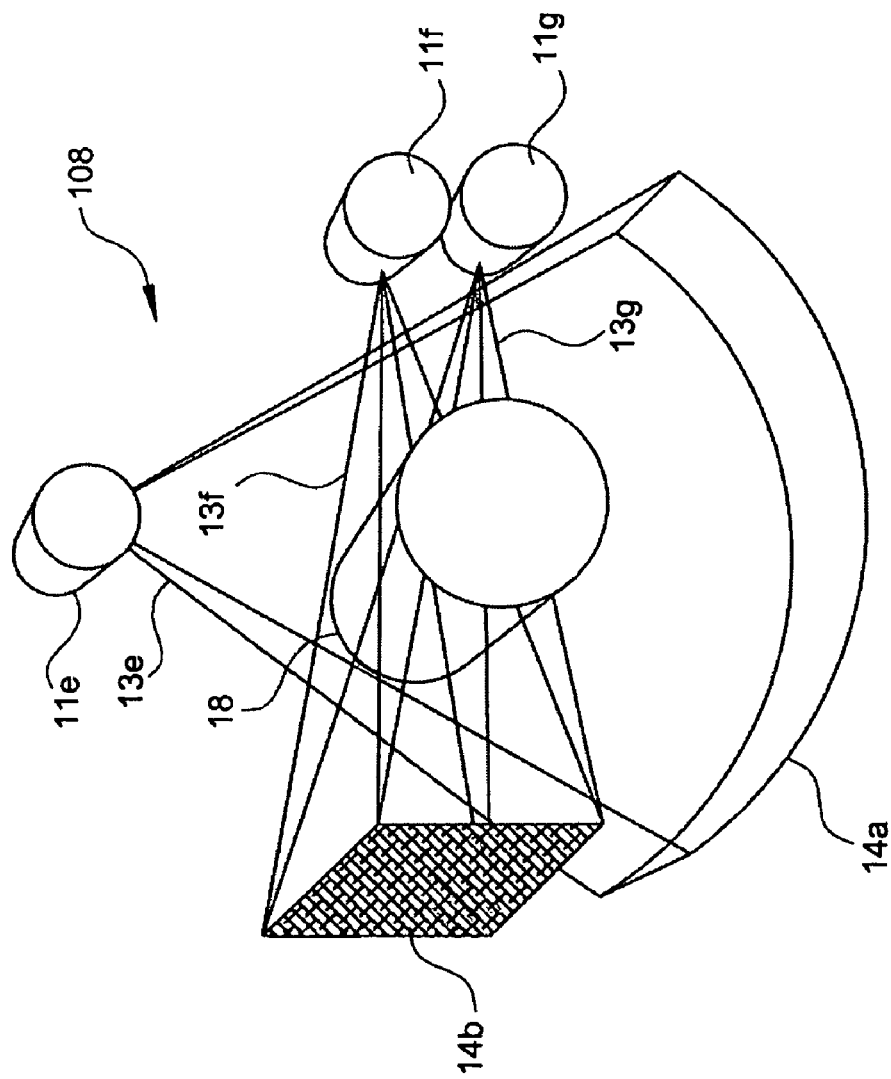

FIG. 5 is an illustration of a multiple detector, multiple X-Ray source, CT scanner according to yet another exemplary embodiment of the current invention, wherein X-Ray sources 11f and 11g are displaced from each other along the X direction and X-Ray source 11e is angularly displaced by 90° relative to sources 11f and 11c.

Figure 6:
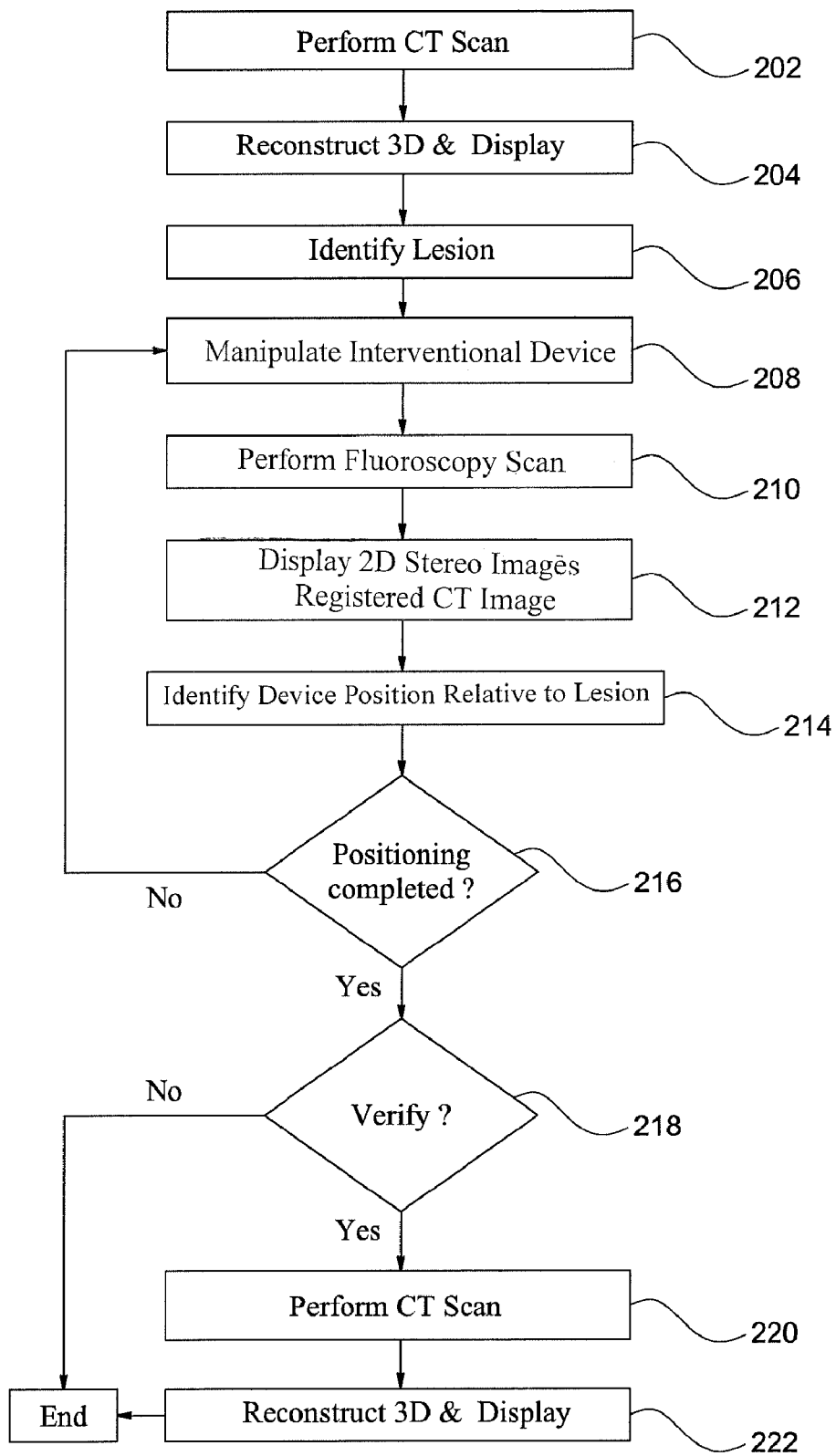

FIG. 6 is a description of a method of using a multiple X-Ray source CT in an interventional procedure according to an exemplary embodiment of the current invention.

DETAILED DESCRIPTION OF THE INVENTION

The invention relates to tracking position of organs, lesions or devices in the human body, and more specifically it relates to application of Computed Tomography (CT) and Stereoscopic Fluoroscopy imaging techniques during interventional procedures.

Before explaining the embodiments of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In discussion of the various figures described herein below, like numbers refer to like parts. The drawings are generally not to scale.

For clarity, non-essential elements were omitted from some of the drawings.

FIG. 1 is a schematic illustration of a prior art cone beam CT scanner 102. X-Ray source, such as X-Ray tube 10 emits a beam of X-radiation 12 in the direction of detector array 14. Typically the source-detector pair is mounted on a rotating gantry and a subject to be examined 18 is positioned between the source and the detector. A collimator is used to shape the beam to a pyramid shape so as to cover the detector area. Detector array 14 may be composed of array of discrete elements arranged in rows and columns, a flat panel detector or the like. Detector array 14 may optionally have a spherical shape or planar shape, or have other surface curvature. Detector array 14 may, as shown for illustrations in these figures have an arc shape (a section of a cylinder) centered about the focal spot. Herein below we refer to "rows" of the detector array, as the row of detector elements in the X direction of the detector, perpendicular to the rotation axis (Z direction).

The coordinate system shown in FIG. 1 refer to the rotating gantry such that the Z axis is parallel to the rotation axis, and the Y axis points from the center of detector array to the X-Ray source at any rotation angle.

Various parts of CT scanner 102, including the gantry, X-Ray source collimator for shaping the X-Ray beam, patient support, data acquisition system, controller, image processor, display unit and other parts are not shown in FIG. 1 and subsequent figures for clarity. However, a person skilled in the art will appreciate that these parts are included in the described embodiments and are operative as a part of the embodiments.

CT scanner 102 acquires data while the gantry rotates around the subject 18, acquiring multiple two dimensional data sets at different rotation angles. A three dimensional tomographic image is than reconstructed using cone beam reconstruction algorithms as known in the art.

FIG. 2 is an illustration of a cone beam CT scanner 104 having multiple X-Ray sources, wherein the sources are displaced from each other along the Z direction according to an exemplary embodiment of the current invention.

X-Ray sources 11a and 11b emit X-Ray beams 13a and 13b, respectively. Beams 13a and 13b are attenuated by subject 18 and impinge on detector array 14. Beams 13a and 13b are overlapping within at least a certain volume of subject 18.

In one mode of operation, CT scanner 104 may optionally be used to generate rotational CT images using both X ray sources as described e.g. in applications US 2006/285633 A1 to Sukovic et. al., WO 2006/038145 A to Koken at. al., or WO 2008/122971 A1 to Dafni. Alternatively, CT scanner 104 may optionally be used to generate rotational CT images using one X-Ray source. CT images may be acquired in any scan mode known in the art, by a single shot, in "step and shoot" mode or by spiral (helical scanning).

In a second mode of operation, the gantry of CT scanner 104 may be stationary at a desired rotation angle and subject 18 may be imaged by 2D projection imaging using X-Ray sources 11a and 11b and detector 14. In this mode the data acquisition system, image processor and display system are operative similar to a digital radiography or a digital fluoroscopy system.

It should be noticed, that the two-dimensional (2D) image detected by array 14 in response to X-Ray beam propagating through subject 18 is a projection of the three-dimensional (3D) distribution of the tissue density of subject 18, as seen from the view-point of the X-Ray source. Thus, images created when source 11a is operational, are slightly different than the images detected when source 11b is operational. By sequentially operating both X-Ray sources, one at a time, stereoscopic views of the 3D subject 18 may be obtained. By electronically controlling the sources 11a and 11b, the time difference between acquiring two images, one using X-Ray beam 13a and the other using X-Ray beam 13b may be short, minimizing or eliminating movement of the subject 18 between the two images acquisition. By a way of non limiting examples, each of sources 11a and 11b may be operated for example 15 or 25 or 30 or 60 times a second, for a pulse duration of for example 1 or 5 or 10 or 15 milliseconds each. However, other pulse frequencies and durations may be used.

In some embodiments, X-Ray sources 11a and 11b are two separate X-Ray tubes.

In other embodiments, sources 11a and 11b are two X-Ray sources within one vacuum enclosure.

In some exemplary embodiments, the sources are associated with separate pairs of anodes and cathodes for each source.

In some exemplary embodiments, the sources are associated with a single anode and cathode arrangement wherein switching between source positions is accomplished by magnetic or electric deflection of electron beam from the cathode. Fast switching of the radiation on and off and between the sources may optionally be achieved by methods known in the art such as pulsing the high voltage supply energizing the X-Ray sources or by application of grids. A person skilled in the art will appreciate there are other methods to provide multiplicity of X-Ray sources spaced apart and to pulse the radiation and such other methods are covered by the current invention.

It should be noted that since generally the two X-Ray sources are working one at a time, one high voltage generator may optionally be used for both sources.

In contrast to acquisition of stereoscopic views, where the gantry is stationary, and sources 11a and 11b are alternation their operation; as described above a CT image may be obtained by rotating the gantry and using one of sources 11a and 11b. Alternatively a third, CT dedicated X-Ray source (not seen in these figures) may be used for acquiring CT data.

System 104 is useful for embodiments of the present invention as described hereinbelow.

FIG. 3 is a side view of a cone beam CT scanner having multiple X-Ray sources 104, wherein the sources are displaced from each other along the Z direction according to an exemplary embodiment of the current invention, showing the scanned subject 18 shown by a way of example a human patient undergoing imaging of the heart.

For clarity, X-ray sources 11a and 11b are represented in this figure by their X-Ray focal points 11a' and 11b'

Striped region 20 marks the volume of the examined region wherein the beams 13a and 13b overlap. Stereoscopic images of the overlapping region 20 may be obtained while the gantry is stationary.

FIG. 4 is an illustration of a multiple X-Ray source, cone beam CT scanner 106 according to another exemplary embodiment of the current invention, wherein X-Ray sources 11c and 11d are displaced from each other along the X direction.

In contrast to the embodiment depicted in FIGS. 2 and 3, X-Ray sources 11c and 11d are displaced from each other along the X direction. X-Ray sources 11c and 11d emit beams of X-radiation 13c and 13d, respectively, beam 13c and 13d, are attenuated by subject 18 and impinge on detector array 14. Beams 13c and 13d are overlapping within at least a certain volume of subject 18. System 106 is useful for embodiments of the present invention as described hereinbelow.

It should be noted, that stereoscopic viewing requires acquisition two images from viewpoints separated by a substantial angular separation. Thus, more than two sources may be used, and a pair of images selected for stereoscopic viewing. It should be noted that the separation of the two X-Ray sources may optionally be at a direction other than purely along the X or the Y axis, for example along the vector {A*X, B*Y} where A and B are arbitrary scalars.

FIG. 5 is an illustration of a multiple detector, multiple X-Ray source, CT scanner 108 according to yet another exemplary embodiment of the current invention, wherein X-Ray sources 11f and 11g are displaced from each other along the X direction and X-Ray source 11e is angularly displaced by 90° relative to sources 11f and 11c.

In contrast to the embodiment depicted in FIGS. 2 3 and 4, system 108 comprises a CT subsystem comprising an X-Ray source 11e and a CT detector 14a. The CT subsystem may be a conventional CT subsystem comprising a fan beam source and a single slice detector 14a. Alternatively, detector 14a may be a multi slice detector having multiple rows of detector elements as known in the art. A 3D CT image may be acquired by helical or step and shoot scanning by advancing the patient table or by translating the gantry or by a single shot providing the detector is wide enough. The CT images are made to overlap stereo fluoroscopic images acquired by fluoroscopic subsystem comprising detector 14b and X-Ray sources 11f and 11g.

Fluoroscopic detector 14b is illuminated by at least two X-Ray sources 11f and 11g producing the at least two cone beams 13f and 13g respectively.

In the depicted embodiment, X-Ray sources 11f and 11g are displaced from each other along the X direction. However, it should be noted that X-Ray sources 11f and 11g may be oriented along the Z axis or along an arbitrary axis.

X-Ray sources 11f and 11g emit cone beams of X-radiation 13f and 13g, respectively, beam 13f and 13g, are attenuated by subject 18 and impinge on detector array 14b. Beams 13f and 13g are overlapping within at least a certain volume of subject 18. Fluoroscopic detector 14b may be a flat detector or a curved detector. It should be noted that the combination of sources 11g and 11f and detector 14b may be optimized for fluoroscopic imaging while the combination of source 11e and detector 14a may be optimized for CT imaging.

In the depicted embodiment, CT subsystem is oriented substantially perpendicular to the fluoroscopic subsystem, however, other orientations may be used. For example, the CT subsystem and the fluoroscopic subsystem may be installed on two independent rotors. For example the two rotors may be located on two opposite sides of the same gantry stator. Subject 18 may be at the same position for the CT and fluoroscopic imaging or may be translated between the two modes of imaging in as long the relative position is registered.

System 108 is useful for embodiments of the present invention as described hereinbelow.

Exemplary embodiments according to the present invention make use of a multiple source CT scanner such as system 104 106 or 108, capable of producing volumetric CT images. Further, the systems in exemplary embodiments are preferably capable of generating stereoscopic fluoroscopy images. By fluoroscopy we refer to multiple X-Ray projection imaging per second. By angiography we refer to fluoroscopy imaging of the cardiovascular system assisted by injection of contrast agent (Dye). Optionally embodiments of the present inventions are used in connection with injection of contrast agent. Stereoscopic images are generated wherein the gantry is positioned at a certain rotation angle and the sources are made to irradiate the subject 18 alternatively. Typically each source generates 15 or 25 or 30 pulses a second although higher lower or other rates are also possible. Optionally, a single shot by each source is preferably used to generate a single stereoscopic radiographic image. Optionally, data from a plurality of images is combined to improve image quality. The common detector 14 of system 104 or 106 (14b in system 108) is operative to receive separately attenuation images for each source. The reconstruction and display of the stereoscopic images are described hereinbelow.

Data provided by detector array 14 (14b for system 108) is preferably computer-processed using conventional techniques known in the field of X-Ray fluoroscopy to generate real time planar image data for each of beams 13a and 13b, for example respective of system 104, (and similarly beams 13c and 14d for system 106; beams 13f and 13g for system 108). According to the invention, the two images are optionally employed to create a composite stereo image for viewing by an operator. The stereo image may be used by the operator to position an interventional device, such as a catheter, angioplasty balloon, stent and the like, relative to a lesion in the patient body as described below.

For stereo visualization, the computer generated planar stereo component images are arranged to be viewed separately by the left and right eyes of an operator so that the two separate images are integrated by the operator's brain into a three-dimensional image. An offset of between about four degrees and ten degrees, preferably between four and seven degrees, for example, about six degrees, yields good results. However, other values of angular separation between the two viewpoints used for generating the stereoscopic images may be used.

Many ways are known for presenting spaced image data to create a stereoscopic effect, and any suitable presentation method may be employed. For example, the separate images may be viewed using a head mounted electro-optically switched viewer, e.g., of the kind shown in. U.S. Pat. No. 4,214,267 to Roese et al, the content of which is incorporated herein by reference. In such an arrangement, separate viewing windows are provided for each eye. The two images are displayed on a single monitor in alternating fashion, but the viewing windows are alternatively blocked in synchronization with the alternating images so one image is viewable only by the left eye, and the other image is viewable only by the right eye.

Alternatively, separate monitors may be provided in a head-mounted viewer to display only one image for each eye.

Another option is to employ the so-called "autostereo" display technology. As known to those skilled in the art, this is a conventional technology in which a single monitor is designed to display two images in such a way that one image is visible only to the left eye, and the other image is visible only to the right eye. Several ways to implement this are known, and autostereo monitors are available commercially from several sources (e.g. Sharp Corp. 3D LCD; and QinetiQ Group PLC, 85 Buckingham Gate, London SW1E 6PD).

Some exemplary embodiments of the present invention acquire substantially simultaneous fluoroscopic images from two sources but do not actually display stereoscopic images. In these embodiments the stereoscopic images are optionally displayed side by side. Optionally, computer algorithm is used to estimate the depth of a feature seen in 2D fluoroscopy images within the 3D volume based on the differences between the two fluoroscopic images and the known system geometry. In these exemplary embodiments the angular separation between the viewpoints is optionally increased compared to embodiments used for stereoscopic visualization. Optionally, each fluoroscopic X-Ray source may be associated with a separate X-Ray detector.

FIG. 6 is a description of a method of using a multiple X-Ray source CT such as system 104, 106 or 108, in an interventional procedure according to an exemplary embodiment of the current invention.

According to an exemplary method of the current invention, system 104 106 or 108 is first used 202 to acquire CT images of a volume of interest. The system than reconstruct and display 204 the volumetric data. The CT images may be acquired responsive to radiation from a single X-Ray source or multiple X-Ray sources. It is to be understood that CT volumetric data is typically image processed by methods known in the art for optimal visualization of the tissues of interest, for example parts of the cardiovascular system. CT images may be visualized as a rendered 3D volume, 3D surface rendered, 2D slices in any orientation, slab of such slices or any other visualization method known in the art. Alternatively or additionally other known image enhancement methods may be used such as: contrast enhancements edge enhancement; image smoothing and filtering; and using false colors.

The operator determines 206 the location of the lesion of interest within the scanned volume and optionally marks the lesion on at least one image by graphic overlay.

Subsequently the operator initiates interventional procedure 208 involving insertion of at least one device to the patient body. One example for such interventional procedures is cardiac catheterization wherein the lesions of interest might be stenoses in the coronary arteries and the devices of interest might be guide wires, catheters, balloons, stents, IVUS probes and the like. Another example for such interventional procedure is needle biopsy wherein the lesion of interest is a suspected tumor and the device of interest might be a biopsy needle. Many other interventional procedures and variations thereof are known in the art and are covered by this invention. The tracked devices might be tools used in the procedure and removed from the body at the end of the procedure, such as catheters and biopsy needles. The tracked devices might also be devices implantable in the body such as percutaneous implantable aortal valves, pacemaker leads, stents, brachytherapy seeds, orthopedic devices and the like.

Generally, interventional procedure 208 is performed under prior art fluoroscopy viewing with or without prior CT imaging. According to the current invention fluoroscopy 210 is used following CT imaging within the same session.

The CT imaging (202) and subsequent fluoroscopy imaging (210) may be assisted by injection or infusion of contrast agent (dye) or may be performed without contrast agent.

In order to track the position of the interventional device, the operator is positioning the gantry having multiple X-Ray sources system 104, 106 or 108 in a suitable angle respective of the patient and operates the system in fluoroscopy mode 210. The operation of the system in fluoroscopy mode is described in FIGS. 2, 3, 4 and 5. Fluoroscopic images may be generated and displayed to the operator in real time as the procedure proceeds. Fluoroscopic images may be dynamically displayed 15 or 25 or 30 times a second or at a different rate or a single fluoroscopic image may be acquired and displayed at a time. Alternatively, a single shot image may be displayed. The operator may choose to change the gantry angle during the procedure. Fluoroscopic images may be displayed side by side or optionally displayed in stereoscopic form as described herein above.

In addition the fluoroscopy images may be displayed overlaid over the 3D CT image 212 so that the operator can appreciate 214 the position of the device relative to the organ and the lesion of interest. Optionally, different colors are used for the CT and fluoroscopy images to enable the user to differentiate between the two overlaid images. Alternatively the fluoroscopy images may be displayed side by side with the CT images wherein overlaid graphic markers indicate same positions on the two sets of images. Graphic mark may be positioned manually by the operator at the device position on the fluoroscopy image and displayed automatically on the CT images. Alternatively or additionally, an algorithm is used for detecting the position of the device in the fluoroscopy images and automatically overlaying it over the CT images as a graphic mark. In exemplary embodiments, algorithm for detecting position of a device in the 3D volume is based on the stereoscopic nature of the fluoroscopy images and the position of the device as appears in the pairs of fluoroscopy images corresponding to two different source viewpoint. Optionally such algorithms are used to compute the position of a device tip, radio-opaque marker or a distinct anatomical feature.

Assuming a well defined and identified feature such as needle tip, catheter tip or a radio-opaque marking appears in both projection images it is possible to calculate the position in the 3D volume using trigonometry because each point in the projection images represents a line-of-view in the volume and the intersection of the two lines gives the 3D position of the feature. The calculated location of the feature may be marked on the registered 3D CT image.

If at least two such features are identified on a thin straight instrument such as a needle, the location and direction of the instrument may be calculated and marked on the 3D CT image and on the fluoroscopic images. Similarly, identifying and calculating the location of at lest three points on an instrument is sufficient for calculating location and orientation of an instrument in space. By locating an instrument, an knowing the shape and construction of the instrument, locations of radio-transparent parts may also be calculated and marked on the 3D CT image and on the fluoroscopic images. These calculations may be performed automatically using image processing software known in the art.

It is to be understood that overlaying CT and fluoroscopic images or correlating position in the two sets of images includes optionally translation of images to same coordinate system (registration) and optional remapping of the CT images to correct for sources-detector geometry effects. Positional and angular sensors in the gantry and the patient table enable automatic registration of the fluoroscopic images with the CT reconstructed image. The system controller may be operative to automatically change the viewing direction of the volumetric CT images according to the fluoroscopy imaging angle so the two sets of images will be viewed from same direction respective of the patient.

Accurate positioning of the 2D images respective of the CT images is provided in the inventive system because both CT and fluoroscopy sets of images are acquired at the same session on the same imaging system while the patient is laid on the same support frame. Therefore, there is an accurate geometrical registration between the sets. Optional stereoscopic visualization according to the present invention provides the operator with depth perception, not available with conventional single source fluoroscopy, and better association of the fluoroscopic images with the 3D CT image. Alternatively, the fluoroscopy images are displayed side by side. Optionally, a computer algorithm may be used to correlate the position of a feature in the at least two fluoroscopic images and the CT images more accurately than possible with prior art systems have a single fluoroscopic view direction.

The positioning of the interventional device is iterative, comprising of repeated steps of manipulating the device 208, and stereoscopic fluoroscopy visualization 212, 214. Once the positioning is completed 216, the operator may optionally choose 218 to perform optional verification by repeated CT imaging 220 and viewing 222 the device position in the CT image.

Persons skilled in the art will appreciate that the sequence of operations described in FIG. 5 is provided by a way of example and for various interventional procedures different sequences of operations combining CT imaging and registered stereoscopic fluoroscopy imaging are possible, and are included in the scope of this invention.

Certain organs in the patient body move perpetually even if the patient is still. These include for example the heart motion and breathing motion. According to some exemplary embodiments of the present invention an optional ECG system is provided to monitor the heart cycle phase. CT imaging and fluoroscopy imaging are optionally gated (prospectively or retrospectively) by the ECG so that imaging is done at a phase of minimal motion and at the same phase for the two imaging modes, thereby providing accurate registration. Other types of heart cycle monitors known in the art are also useable in embodiments of the invention.

According to some embodiments of the present invention, the patient is instructed to hold breathing during imaging at a given level of lungs filling (for example maximum or minimum or other level of filling). According to other preferred embodiment a breathing sensor as known in the art is provided and used for gating of the imaging. According to some embodiments, both heart cycle and breathing cycle monitoring gating are provided.

CT systems 104 and 106 with two sources are given by a way of example but systems with a larger number of X-Ray sources may be used as well. Further, multiple source systems with more than two sources may be provided, wherein different pairs of sources may be used for stereoscopic imaging. For example, a single or a multiple X-Ray source may be used for CT imaging and a different pair of sources may be used for stereoscopic imaging.

CT systems 104 and 106 with a single detector are given by a way of example but systems more than one detector may be used as well, as demonstrated by system 108 in FIG. 5. Further, multiple source systems with more than one detector may be provided, wherein one detector associated with multiple X ray sources may be used for stereoscopic imaging and a second detector associated with a single or multiple X ray sources may be used for CT imaging.

The multiple X-Ray sources may be provided as separate X-Ray tubes, a single X-Ray tube housed within one vacuum enclosure wherein said tube has multiple focal spots or by any other technique known in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed:

1. A CT scanner for scanning a subject comprising:
a gantry rotor configured to rotate about the subject;
at least two cone beam X-Ray sources displaced from each other mounted on said gantry rotor;
at least one 2D detector array mounted on said gantry rotor, said detector is operable to receive radiation emitted by said at least two cone beam X-Ray sources and attenuated by the subject;
a first image processor operable to generate CT images of a volume within the subject;
a second image processor operable to generate fluoroscopy images of said volume, wherein said fluoroscopy images are responsive to X-Rays separately emitted by each of said at least two cone beam X-Ray sources and wherein said fluoroscopy images are spatially registered to said CT images; and
a third image processor operable to display said fluoroscopy images responsive to X-Rays separately emitted by each of said at least two cone beam X-Ray sources and said CT images wherein the position of at least one feature within said volume may be visualized simultaneously in said fluoroscopy images and said CT images.

2. A CT scanner according to claim 1, wherein any of said first image processor, second image processor and third image processor are incorporated into a single image processor.

3. A CT scanner according to claim 1, wherein said at least two X-Ray sources are displaced from each other along a direction parallel to the rotation axis of said gantry.

4. A CT scanner according to claim 1, wherein said at least two X-Ray sources are displaced from each other azimuthally respective of the rotation axis of said gantry.

5. A CT scanner according to claim 1, wherein said at least two X-Ray sources comprise two X-Ray sources.

6. A CT scanner according to claim 1, wherein said fluoroscopic images are generated following injection of contrast agent.

7. A CT scanner according to claim 1, wherein said fluoroscopic images are generated and displayed in a sequence selected from a group comprising: multiple times per second; and one image at a time.

8. A CT scanner according to claim 1, wherein said fluoroscopic images are displayed overlaying an image derived from said CT images.

9. A CT scanner according to claim 1, wherein said fluoroscopic images are displayed side by side with said CT images.

10. A CT scanner according to claim 1, wherein a graphic mark indicating position of said at least one feature within said volume is overlaid said CT images.

11. A CT scanner according to claim 1, wherein said fluoroscopic images are used to position an interventional device respective of a lesion or specific anatomic structure.

12. A CT scanner according to claim 11, wherein said lesion or specific anatomic structure is identified using CT images.

13. A CT scanner according to claim 11, wherein the position of said interventional device respective said lesion or specific anatomic structure is verified using CT images, wherein the positioning process is guided by said fluoroscopic images.

14. A CT scanner according to claim 1, wherein said fluoroscopic images are visualized as stereoscopic images.

15. A CT scanner according to claim 14, wherein said stereoscopic images are visualized in a sequence selected from a group comprising: multiple times per second; and one image at a time.

16. A CT scanner according to claim 14, wherein said stereoscopic images are displayed overlaying CT images.

17. A CT scanner according to claim 14, wherein said stereoscopic images are displayed side by side with CT images.

18. A CT scanner according to claim 1, wherein a depth of said at least one feature is computed based on at least two fluoroscopic images acquired from different viewpoints respective the subject.

19. A CT scanner according to claim 1, wherein images are acquired responsive to at least one signal selected from a group comprising: heart monitor signal; and breathing monitor signal.

20. A CT scanner according to claim 1, wherein said multiple X-Ray sources comprise a single X-Ray tube housed within a single vacuum enclosure wherein said tube has multiple focal spots.

21. A CT scanner according to claim 1, wherein said multiple X-Ray sources comprise multiple X-Ray tubes.

22. A CT scanner according to claim 1, wherein the CT scanner comprises more than two sources wherein at least two sources are operative for generating stereoscopic images.

23. A CT scanner for scanning a subject comprising:
a gantry stator;
at least one gantry rotor, mounted on said gantry stator made to rotate about a subject;
a CT subsystem comprising: at least one CT X-Ray source mounted on said at least one rotor; at least one CT X-Ray detector array mounted on said at least one rotor; wherein said at least one CT X-Ray source and said at least one X-Ray detector are configured to rotate together about the subject, and wherein said CT detector array is operable to receive radiation emitted by said CT X-Ray source and attenuated by the subject to be scanned; and a first image processor operable to generate and display CT images of a volume within the subject; and
a fluoroscopy subsystem comprising: at least one first and a second cone beam X-Ray sources displaced from each other mounted on said at least one rotor; a 2D detector mounted on said at least one rotor, wherein said at least one first and a second cone beam X-Ray sources and said 2D detector array are configured to rotate together about the subject to be scanned, and wherein said 2D detector is capable of receiving radiation emitted by said at least one first and second X-Ray sources and attenuated by the subject to be scanned; and a second image processor capable of generating projection X-Ray images of said volume, wherein the images are responsive to X-Ray separately emitted by each of said at least one first and second cone beam X-Ray sources; and a third image processor capable of generating and displaying fluoroscopic images composed of said projection X-Ray images, wherein said fluoroscopic images are spatially registered to said CT images.

24. The CT scanner of claim 23, wherein said CT subsystem and said fluoroscopy subsystem are mounted on the same gantry rotor.

25. The CT scanner of claim 23, wherein said CT subsystem and said fluoroscopy subsystem are mounted substantially perpendicular to each other.

26. The CT scanner of claim 23, wherein said at least one gantry rotor comprises a first and a second gantry rotors configured to independently rotate about the subject, and wherein said CT subsystem is mounted to said first gantry rotor, and said fluoroscopy subsystem is mounted on said second gantry rotor, and wherein said first and second gantry rotors are mounted on said gantry stator.

27. A CT scanner according to claim 23, wherein said fluoroscopic images are visualized as stereoscopic images.

28. A CT scanner according to claim 23, wherein a graphic mark indicating position of a feature within said volume is overlaid said CT images wherein said position of the feature within said volume is computed responsive to the position of the feature in said projection X-Ray images.

29. A CT scanner for scanning a subject comprising:
a gantry rotor configured to rotate about the subject;
at least two cone beam X-Ray sources displaced from each other mounted on said gantry rotor;
at least one 2D detector array mounted on said gantry rotor, said detector is operable to receive radiation emitted by said at least two X-Ray sources and attenuated by the subject;
a first image processor operable to generate and display CT images of a volume within the subject;
a second image processor operable to generate and display fluoroscopy images of said volume, wherein said fluoroscopy images are responsive to X-Rays separately emitted by each of said at least two cone beam X-Ray sources and wherein said fluoroscopy images are spatially registered to said CT images; and
a third image processor operable to track the spatial position of at least one feature within said volume responsive to the position of the at least one feature in said fluoroscopy images.

30. A CT scanner according to claim 29, wherein any of said first image processor, second image processor and third image processor are incorporated into a single image processor.

31. A CT scanner according to claim 29, wherein said at least two X-Ray sources are displaced from each other along a direction parallel to the rotation axis of said gantry.

32. A CT scanner according to claim 29, wherein said at least two X-Ray sources are displaced from each other azimuthally respective of the rotation axis of said gantry.

33. A CT scanner according to claim 29, wherein said at least two X-Ray sources comprise two X-Ray sources.

34. A CT scanner according to claim 29, wherein said fluoroscopic images are generated following injection of contrast agent.

35. A CT scanner according to claim 29, wherein said fluoroscopic images are generated and displayed in a sequence selected from a group comprising: multiple times per second; and one image at a time.

36. A CT scanner according to claim 29, wherein said fluoroscopic images are displayed overlaying an image derived from said CT images.

37. A CT scanner according to claim 29, wherein said fluoroscopic images are displayed side by side with said CT images.

38. A CT scanner according to claim 29, wherein a graphic mark indicating position of said at least one feature within said volume is overlaid said CT images.

39. A CT scanner according to claim 29, wherein said fluoroscopic images are used to position an interventional device respective of a lesion or specific anatomic structure.

40. A CT scanner according to claim 29, wherein said fluoroscopic images are visualized as stereoscopic images.

41. A CT scanner according to claim 29, wherein tracking the spatial position of at least one feature comprise computation of the depth of said at least one feature in said volume based on at least two fluoroscopic images acquired from different viewpoints respective the subject.

42. A CT scanner according to claim 29, wherein images are acquired responsive to at least one signal selected from a group comprising: heart monitor signal and/or breathing monitor signal.

43. A CT scanner according to claim 29, wherein the CT scanner comprises more than two sources wherein at least two sources are operative for generating stereoscopic images.

44. A CT scanner according to claim 30, wherein said stereoscopic images are visualized in a sequence selected from a group comprising: multiple times per second; and one image at a time.

45. A CT scanner according to claim 30, wherein said stereoscopic images are displayed overlaying CT images.

46. A CT scanner according to claim 30, wherein said stereoscopic images are displayed side by side with CT images.

* * * * *